(12) United States Patent
Gundel et al.

(10) Patent No.: US 7,294,246 B2
(45) Date of Patent: Nov. 13, 2007

(54) ELECTRODE FOR ELECTROCHEMICAL SENSORS

(75) Inventors: Douglas B. Gundel, Austin, TX (US); Dennis M. Brunner, Centralia, MO (US)

(73) Assignee: 3M Innovative Properties Company, St. Paul, MN (US)

( * ) Notice: Subject to any disclaimer, the term of this patent is extended or adjusted under 35 U.S.C. 154(b) by 566 days.

(21) Appl. No.: 10/702,828

(22) Filed: Nov. 6, 2003

(65) Prior Publication Data

US 2005/0098434 A1    May 12, 2005

(51) Int. Cl.
G01N 27/327    (2006.01)
G01N 27/403    (2006.01)
(52) U.S. Cl. .................. 204/403.14; 204/400
(58) Field of Classification Search ............................... 204/403.01–403.15, 400
See application file for complete search history.

(56) References Cited

U.S. PATENT DOCUMENTS

| | | | |
|---|---|---|---|
| 4,778,758 A | 10/1988 | Ericsson et al. | |
| 4,897,173 A | 1/1990 | Nankai et al. | |
| 5,288,636 A | 2/1994 | Pollmann et al. | |
| 5,437,999 A | 8/1995 | Diebold et al. | |
| 5,741,634 A | 4/1998 | Nozoe et al. | |
| 5,762,770 A | 6/1998 | Pritchard et al. | |
| 5,820,957 A | 10/1998 | Schroeder et al. | |
| 5,981,203 A | 11/1999 | Meyerhoff et al. | |
| 5,997,817 A | 12/1999 | Crismore et al. | |
| 6,096,247 A | 8/2000 | Ulsh et al. | |
| 6,175,752 B1 | 1/2001 | Say et al. | |
| 6,287,451 B1 | 9/2001 | Winarta et al. | |
| 6,893,545 B2 * | 5/2005 | Gotoh et al. | 204/403.04 |
| 6,923,894 B2 * | 8/2005 | Huang et al. | 204/403.06 |
| 2002/0092612 A1 | 7/2002 | Davies et al. | |
| 2003/0088166 A1 | 5/2003 | Say et al. | |
| 2003/0102213 A1 | 6/2003 | Gotoh et al. | |
| 2003/0200644 A1 | 10/2003 | Matzinger | |
| 2003/0203498 A1 | 10/2003 | Neel et al. | |

FOREIGN PATENT DOCUMENTS

| | | |
|---|---|---|
| DE | 44 27 363 A1 | 3/1995 |
| DE | 100 20 445 A1 | 11/2001 |
| EP | 1 152 239 A1 | 11/2001 |
| EP | 1 203 823 A1 | 5/2002 |
| JP | 05-72172 A * | 3/1993 |

(Continued)

OTHER PUBLICATIONS

JPO computer translation of Omron Corp. (JP 05-072172 A), Mar. 23, 1993.*

(Continued)

*Primary Examiner*—Alex Noguerola
(74) *Attorney, Agent, or Firm*—Melanie G. Gover

(57) ABSTRACT

Provided are electrochemical circuits with electrodes having a main body section and at least one neck section wherein the width of at least a portion of the neck section is less than the width of the narrowest portion of the main body section, and an insulative layer over a portion of the conductive layer such that at least a portion of an electrode neck section is not covered by the insulative layer. Also provided are methods of making the electrochemical circuits.

16 Claims, 3 Drawing Sheets

FOREIGN PATENT DOCUMENTS

| | | | |
|---|---|---|---|
| JP | 11-304748 A | * | 11/1999 |
| WO | WO 99/13099 | | 3/1999 |
| WO | WO 01/25775 A1 | | 4/2001 |
| WO | WO 02/00918 A2 | | 1/2002 |

OTHER PUBLICATIONS

JPO computer translation of Nakajima et al. (JP 11-304748 A), Nov. 5, 1999.*

Linder, Erno, Cosofret, Vasile V., Ufer, Stefan and Buck, Richard P.; Kusy, Robert P.; Ash, R. Bruce and Nagle, H. Troy, "Flexible (Kapton-based) Microsensor Arrays of High Stability for Cardiovascular Applications", J. Chem. Soc. Faraday Trans., 1993, vol. 89, pp. 361-367.

Co-pending U.S. Appl. No. 10/702,827, Douglas B. Gundel, filed Nov. 6, 2003.

Co-pending U.S. Appl. No. 10/702,344, Douglas B. Gundel, filed Nov. 6, 2003.

International Search Report for PCT/US2004/033525, mailed Feb. 15, 2005.

* cited by examiner

ELECTRODE FOR ELECTROCHEMICAL SENSORS

TECHNICAL FIELD

This invention relates to electrochemical sensors that are used to quantitatively assess the concentration of a given analyte in a solution.

BACKGROUND

Electrochemical sensors such as biosensors have been used for many years. Among other applications, they now play an important role in the daily monitoring of blood glucose levels in diabetic patients, who sometimes perform four or more measurements per day. Once the glucose level is determined, action regarding adjustment of the insulin or glucose level in the blood is initiated. Serious and life-threatening consequences can result if the patient's blood glucose falls too low or becomes too high. Beyond the benefits of alerting a patient to the extremes, controlling blood glucose levels is considered to reduce incidence reduction of kidney, nerve, and retinal damage that can otherwise result from poor control. Clearly, the accuracy of the electrochemical measurements is critical to the health and well-being of the patient.

Known electrochemical sensors typically comprise a planar substrate, a working electrode and a counter or reference electrode on the substrate, a reagent comprising an enzyme and mediator on the working electrode, and a means for transporting the fluid sample to the electrode surface. The electrodes are arranged so that a signal representing the analyte concentration can be generated. The measurement technique is typically amperometric where a known voltage is applied and current is generated by the biochemical reaction (e.g., glucose reaction) and measured by an electronic device (meter). These reactions usually include an initial reaction with the enzyme that is selective for an analyte (e.g., glucose) in a sample, and a mediator that shuttles electrons between the enzyme and a working electrode. In this case, the sensor includes at least one counter or reference electrode and one working electrode. The reactant layer also can include other components that participate in the reaction or perform other functions. Other measurement techniques mentioned in the literature are coulometric and voltametric methods.

SUMMARY

One embodiment of the present invention features a novel article comprising an electrochemical sensor comprising a substrate, a conductive layer comprising at least one electrode having a main body section and at least one neck section wherein the width of at least a portion of the neck section is less than the width of the narrowest portion of the main body section, and an insulative layer over a portion of the conductive layer such that at least a portion of an electrode neck section is not covered by the insulative layer.

Another embodiment of the present invention features a novel method for minimizing variations in the surface area of an electrode comprising placing on a substrate a pattern of conductive material to form at least one electrode having a main body section and at least one neck section, wherein the width of at least a portion of the neck section is less than the width of the narrowest portion of the main body section, and placing over the conductive material a pattern of insulative material that forms an opening wherein at least a portion of a neck section is exposed, a neck section being of sufficient length that the placement accuracy of the insulative material with respect to the main electrode body can vary without the variance causing the insulative material to cover all of or none of the neck.

As used in this invention:

"connection neck" means a narrowed portion of a conductive layer that extends from the main body of an electrode to the conductive trace.

"termination neck" means a narrowed portion of a conductive layer that extends from the main body of the electrode and terminates without connecting the electrode to any other conductive element of a circuit.

An advantage of at least one embodiment of the present invention is that, for an electrode whose surface area is defined by patterned conductive and insulative layers, it can increase the accuracy of defining the electrode surface area when the conductive layer patterning is more accurate than the insulative layer patterning. This translates directly to an increased measurement accuracy of the system. Increased accuracy may also result in reduced manufacturing costs and improved yields.

Another advantage of at least one embodiment of the present invention is that the analyte sample size may be decreased as a result of the more tightly controlled electrode area.

Other features and advantages of the invention will be apparent from the following drawings, detailed description, and claims.

DETAILED DESCRIPTION

Figure 1:
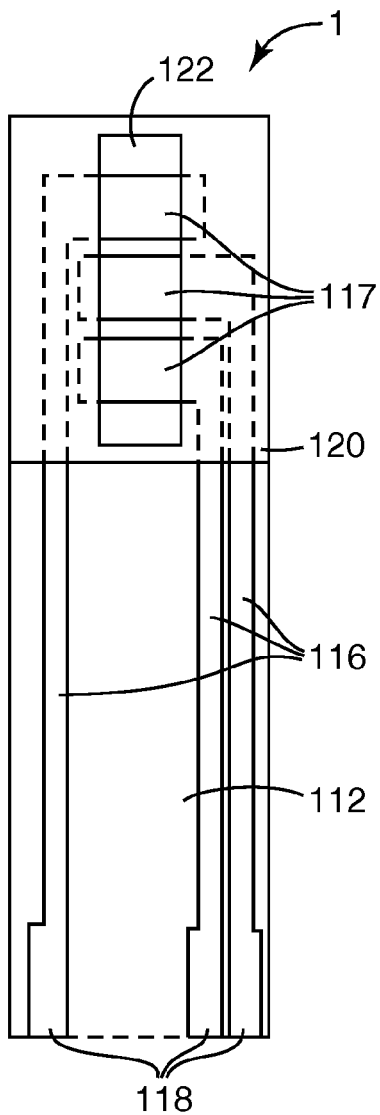
FIG. 1 depicts a prior art multi-electrode sensor circuit.

Sensor circuit 1, of FIG. 1, is a typical disposable electrochemical sensor for blood glucose monitoring. Sensor circuit 1 includes substrate film 112 on which is deposited a layer of conductive material that is patterned to form electrodes 117 (including working electrodes, reference electrodes, dummy electrodes, or redundant electrodes), traces 116 and contact pads 118. The traces are the portions of the conductive layer that connect the electrodes to contact pads. The traces may be any size or shape.

A further functional structure that is usually added is a covercoat, or insulative layer 120, which forms a window 122 over a portion of the conductive layer. Contact pads 118 are needed so that electrical contacts can be made when the sensor is inserted into a meter (not shown). Because the insulative layer defines the area of the conductive layer that can collect a signal, and can also define the analyte sample volume in some instances, it can directly influence the accuracy of the reading. The insulative layer may be screen-printed, photolithographically patterned, or laminated over the conductive layer.

At least one embodiment of the present invention can decrease the size of electrodes and increase the accuracy of the defined electrode surface area compared to prior art electrodes, the surface areas of which are typically defined by either conductive layer patterning or insulative layer patterning and registration. This in turn can increase the accuracy of the sensor measurement compared to prior art electrodes (until other factors dominate the measurement variability).

Some aspects of the present invention are particularly useful with construction methods in which the conductive layer is more accurately patterned than the insulative layer. Aspects of the invention limit the effect of the insulative layer patterning on electrode area and size accuracy. This will enable the industry to continue to pattern the insulative layer using a low cost, low accuracy process while increasing electrode area accuracy. Alternatively, it can provide an even more accurate electrode with an improved insulative layer patterning process. Both of these are clear benefits to the manufacture and use of the resulting electrochemical sensor.

At least one embodiment of the invention provides for an electrode having a main body section and at least one "neck" section having a narrower width than the main body of the electrode. The neck section may connect the main body section to another conductive element of the circuit, or may terminate without connecting to any other element. FIGS. 2a-2f show exemplary electrode shapes of the present invention. The electrodes have main electrode body sections 224 and one or both of a connective neck 226 and a terminal neck 228. As is illustrated by the various examples, an electrode of the present invention has a neck on at least one side. Additionally, the necks may have various shapes. For example, they may be straight, as shown in, e.g., FIG. 2a, tapered as shown in FIG. 2d, scalloped, rounded, curved, square, rectangular, etc. The main electrode body sections of adjacent electrodes may be off-set as illustrated in FIG. 2c, or aligned as illustrated in FIGS. 2a, 2b, and 2d-2f.

An important advantage of at least one embodiment of the invention is that an edge of the insulative layer that defines a side of window 222 intersects an electrode at least at one neck section. The necked down section of the electrode reduces the negative effect of imprecise application of the insulative layer on the final electrode surface area. For example, if the insulative layer edges are poorly defined (e.g., jagged, serrated, etc.), the effect of the poor definition is minimized because the width of the neck intersecting the insulative layer edge is so small.

Without the advantage afforded by the present invention, the ability to improve the definition of the electrode shape and size would be limited to improving how the insulative layer is applied, even when the conductive layer patterning is perfect. With the advantage afforded by the present invention, the ability to accurately define the electrode surface area can be more dependent on the conductive layer definition accuracy than the insulative layer definition accuracy. In fact, the present invention allows small electrodes with desired area coefficients of variation (COVs), which is equal to the ratio of the area standard deviation to the area mean, to be made even with poor electrode patterning methods (e.g., screen printing, lamination, etc.). In fact, the electrode area COV for the present invention can approach that of the conductive layer patterning process, regardless of the accuracy of the insulative layer patterning process.

An electrode of the present invention with one or both of a connective neck and a terminal neck can compensate for placement inaccuracies of the insulative layer window by keeping the electrode size substantially constant, even if the window is not centered over the main electrode body.

Variations in the COV and or surface area of an electrode can be achieved by patterning a conductive material to form an electrode having a main body section and at least one neck section then placing over the conductive material a pattern of insulative material that forms an opening such that at least a portion of a neck section is exposed. In this case, a neck section should be of sufficient length that the placement accuracy of the insulative material with respect to the main electrode body can vary without the variance causing the insulative material to cover all of or none of a neck section.

Figure 3A:
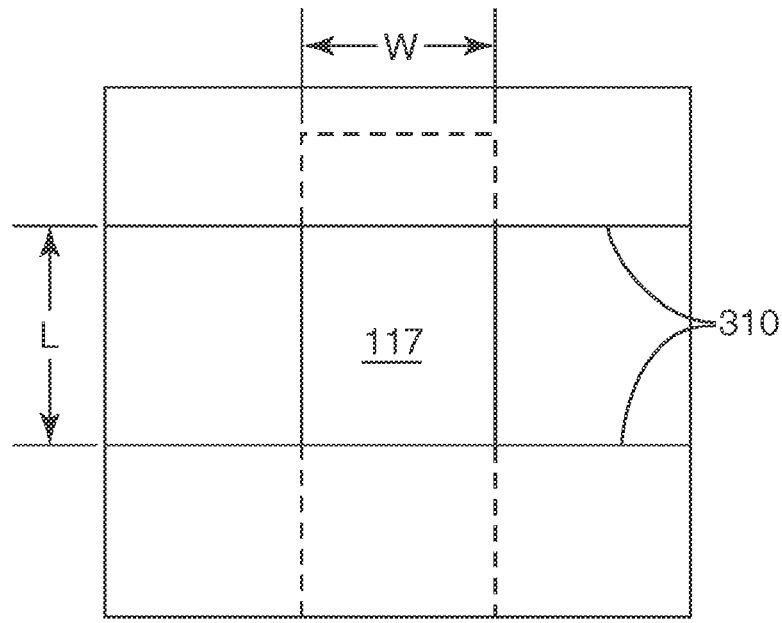
FIG. 3a depicts the dimensions of a prior art electrode defined by patterned conductive and insulative layers.

For a prior art electrode construction (uniform width electrode 117) such as that shown in FIG. 3a, the electrode area (A) is defined by the electrode length (L) as defined by the edges of the insulator window 310 and the electrode width (W):

$$A=WL$$

Propagation of error analysis can be used to show that the variance in electrode area is:

$$\sigma_A^2 = \sigma_W^2 L^2 + \sigma_L^2 W^2$$

where $\sigma_W$ is the standard deviation of electrode width (controlled by conductor patterning process) and is equivalent to the standard deviation of a conductor feature size=$\sigma_{cond}$, $\sigma_L$ is the standard deviation of electrode length (controlled by insulator patterning process) and is equivalent to the standard deviation of an insulator window size=$\sigma_{ins}$, $\sigma_A$ is the standard deviation of electrode area (controlled by both conductor and insulator patterning processes)

The COV of the electrode area is:

$$\frac{\sigma_A}{A} = \frac{\sqrt{\sigma_{cond}^2 L^2 + \sigma_{ins}^2 W^2}}{LW}$$

For example, assuming a required electrode area COV of 5%, and a $\sigma_{cond}$ of 1 µm, a $\sigma_{ins}$ of 15 µm, the minimum value of W and L (assuming for simplicity sake that W=L) is calculated to be 300 µm.

Figure 2A:
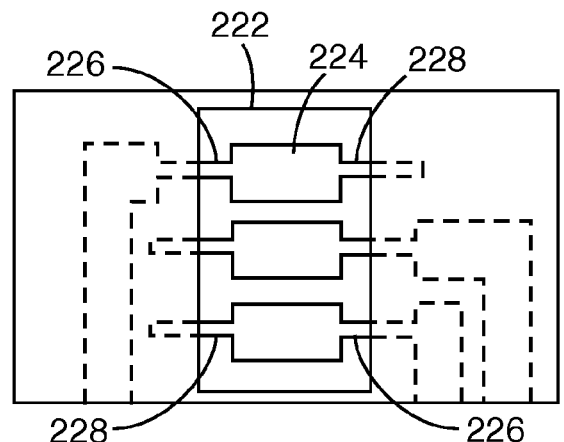
FIG. 2a depicts an embodiment of a multi-electrode sensor circuit of the present invention wherein each electrode has a connection neck and a termination neck.
Figure 2B:
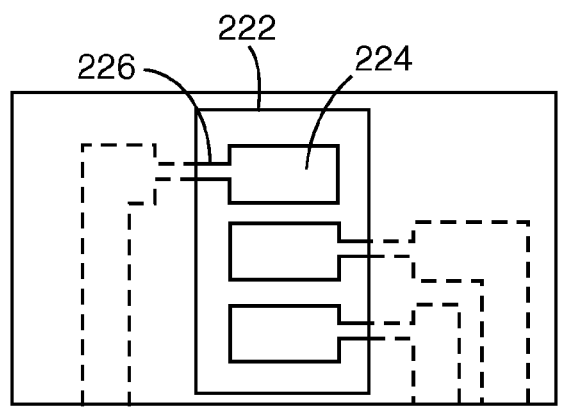
FIG. 2b depicts an embodiment of a multi-electrode sensor circuit of the present invention wherein each electrode has only a connection neck and only one edge of the opening in the insulative layer intersects the conductive layer material.
Figure 2C:
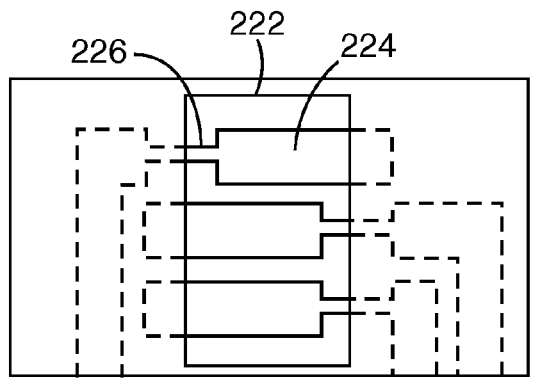
FIG. 2c depicts an embodiment of a multi-electrode sensor circuit of the present invention wherein each electrode has only a connection neck and both side edges of the opening in the insulative layer intersect the conductive layer material.
Figure 2D:
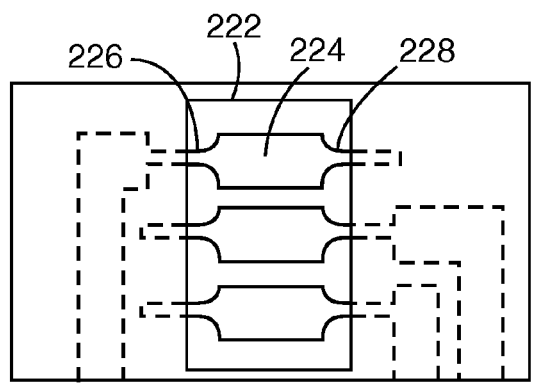
FIG. 2d depicts an embodiment of a multi-electrode sensor circuit of the present invention wherein the electrodes have tapered connection neck and termination necks.
Figure 2E:
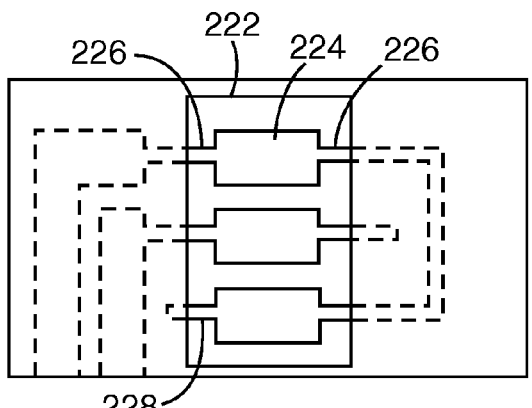
FIG. 2e depicts an embodiment of a multi-electrode sensor circuit of the present invention wherein connective necks join two parts of a complex electrode.
Figure 2F:
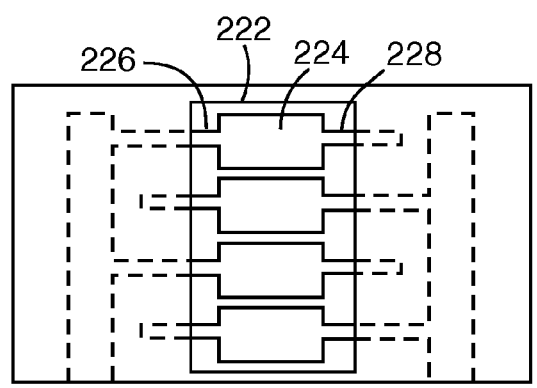
FIG. 2f depicts an embodiment of a multi-electrode sensor circuit of the present invention wherein the electrodes are interdigitated.
Figure 3B:
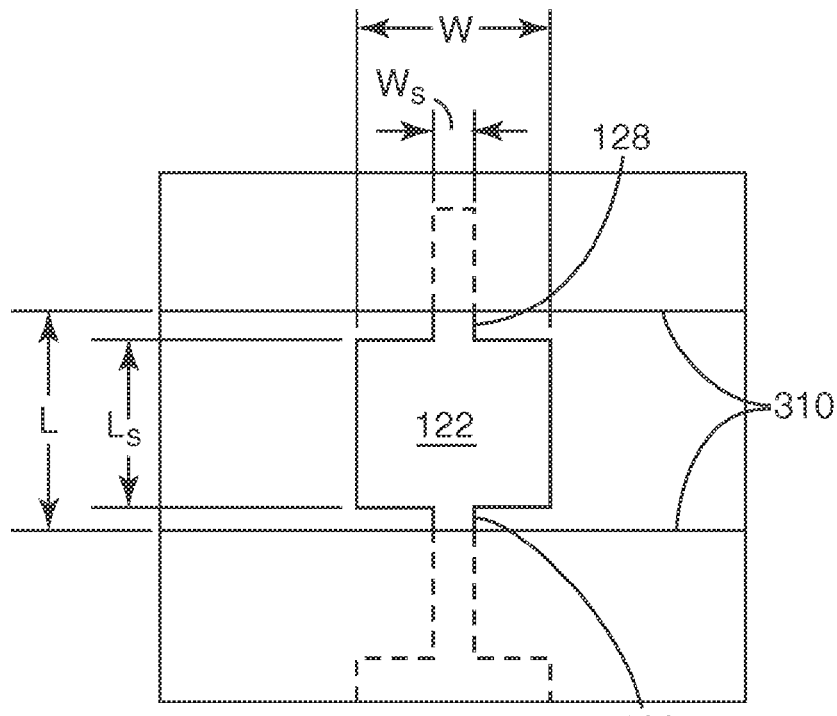
FIG. 3b depicts the dimensions of an electrode embodiment of the present invention defined by patterned conductive and insulative layers.

The advantage provided by at least one aspect of the present invention, which reduces the possible electrode size, while maintaining the same electrode area COV can be demonstrated with the following equations, which describes the electrode of the form shown in FIG. 3b (which may be in the arrangement as shown in FIG. 2a).

For an electrode having one or both of connector and terminal neck sections, the electrode area is:

$$A = L_s W + W_S(L - L_S)$$

where W is the width of the main electrode body 124, $W_s$ is the width of the neck portions 126, 128, (which is assumed to be the same for the connective neck and the terminal neck in this analysis), L is the electrode length as defined by the edges of the insulator window 310, and $L_s$ is the length of the main electrode body.

The variance in the exposed electrode area is:

$$\sigma_A^2 = \sigma_{cond}^2[(W-W_S)^2 + L_S^2 + (L-L_S)^2] + \sigma_{ins} W_S^2$$

Therefore, the COV of exposed electrode area is:

$$\frac{\sigma_A}{A} = \frac{\sqrt{[\sigma_{cond}^2[(W-W_S)^2 + L_S^2 + (L-L_S)^2] + \sigma_{ins}^2 W_S^2}}{[L_s W + W_S(L - L_S)]}$$

Using the same assumptions as in the prior art example above, and assuming that $W/W_S=10$, $L_S/L=0.9$, then the minimum electrode dimension (L or W) that can achieve a COV of 5% is 43 µm (as compared to the 300 µm in the prior art example above). One embodiment of the invention is therefore to reduce the electrode surface area (while maintaining the same electrode COV) and hence reduce the analyte required to make a measurement.

Alternatively, the same equations can be used to demonstrate that for the same electrode size, the exposed electrode COV can be dramatically reduced with the invention. Table 1 shows how embodiments of the present invention can be used to provide a benefit over the prior art in terms of exposed electrode area COV for similarly sized electrodes. This is true especially when the feature size variability for the insulator is much greater than that of the conductor.

Comparative Examples (C. Ex.) 1a and 2a have the dimensions of prior art electrodes (no necked regions) as shown in FIG. 3a. Examples (Ex.) 1b and 2b have the dimension of electrodes of the present invention (necked regions) as shown in FIG. 3b. Using the formulae described above, the COVs for similarly sized electrodes C. Ex. 1a and Ex. 1b are 1.0% and 0.30%, respectively. Comparison of the COVs for similarly sized electrodes C. Ex. 2a and Ex. 2b are 5.0% and 0.62%, respectively. The data in Table 1 indicates that the COV for the electrodes of the present invention are substantially less than that for prior art electrodes.

TABLE 1*

Comparison of Coefficients of Variation for Electrodes Shapes of the Prior Art and of the Invention

| | | W | L | Ws | Ls | A |
|---|---|---|---|---|---|---|
| C. Ex. 1a** | Mean | 1 | 1 | — | — | 1 |
| | Standard Deviation | 0.002 | 0.01 | — | — | 0.01 |
| | Coefficient of Variation | 0.002 | 0.01 | — | — | 1.0% |
| Ex. 1b*** | Mean | 1 | 1 | 0.1 | 0.9 | 0.91 |
| | Standard Deviation | 0.002 | 0.01 | 0.002 | 0.002 | 0.027 |
| | Coefficient of Variation | 0.002 | 0.01 | 0.02 | 0.0022 | 0.30% |
| C. Ex. 2a** | Mean | 1 | 1 | — | — | 1.00 |
| | Standard Deviation | 0.002 | 0.05 | — | — | 0.0500 |
| | Coefficient of Variation | 0.002 | 0.05 | — | — | 5.0% |
| Ex. 2b*** | Mean | 1 | 1 | 0.1 | 0.9 | 0.91 |
| | Standard Deviation | 0.002 | 0.05 | 0.002 | 0.002 | 0.0056 |
| | Coefficient of Variation | 0.002 | 0.05 | 0.02 | 0.002 | 0.62% |

*Dimensions are in Arbitrary Units
**Dimensions are as illustrated in FIG. 3a
***Dimensions are as illustrated in FIG. 3b Electrochemical sensors of the present invention are useful in glucose monitoring systems. The electrochemical sensors can form a portion of a glucose test strip. A glucose test strip typically comprises a planar substrate, a working electrode and a counter or reference electrode on the substrate, a reagent comprising an enzyme and mediator on the working electrode, and a means for transporting the blood sample to the electrode surface. The electrodes are arranged so that a signal representing the glucose concentration can be generated. After a blood sample is applied onto the working electrode, the test strip (or at least the portion of the test strip containing the contact pads) is inserted into a glucose measuring device such as the blood glucose meter available under the trade name ACCUCHEK ADVANTAGE from Roche Diagnostics Corporation, a division of F. Hoffmann-La Roche Ltd, Basel, Switzerland, which provides a read-out of the glucose level in the blood sample. Glucose monitoring systems are often provided in the form of a kit, which can contain test strips, a glucose measuring device, and optionally a lancet for puncturing the skin to produce a blood sample.

Circuits for electrochemical sensors of the present invention can be made using various known procedures such as metal sputtering, plating, resist laminating, resist exposing, developing, and etching. The sequence of such procedures may be varied as desired for the particular application.

One method for making an electrochemical circuit has a typical sequence of steps described as follows:

A dielectric substrate is provided. The dielectric substrate may be a polymer film selected from the group of polyester, polyimide, liquid crystal polymer, polyvinyl chloride, acrylate, polyolefin, polycarbonate, and the like having a thickness of about 10 µm to about 500 µm. The substrate may be coated with a seed layer of chrome, nickel or alloys thereon using a vacuum sputtering or evaporation technique followed by the coating of a first conductive layer. Alternatively, the conductive layer may be deposited directly onto the dielectric substrate. Suitable conductive metals for use in the conductive layer(s) of the present invention include gold (Au), Palladium (Pd), Platinum (Pt), Silver (Ag), Tin (Sn) and alloys thereof. The metal layer is typically about 5 to about 200 nm thick. The conductive layer(s) may be applied by vacuum deposition methods known in the art, such as sputtering or evaporation, or by electroless deposition.

Photoresists, which may be aqueous or solvent based, and may be negative or positive photoresists, are then laminated, or coated, on at least one side of the metal-coated polymeric substrate. Standard hot roller laminating techniques may be used. A suitable dry film is available as SF310 from MacDermid, Inc., Waterbury, Mass. A coated liquid resist can provide a thinner layer than lamination, but is more expensive. The thickness of the photoresist may be from about 1 µm to about 50 µm. The photoresist is then exposed to ultraviolet light or other suitable radiation, through a mask or phototool, which crosslinks the exposed portions of the resist. Suitable energy levels are about 50 mJ/cm$^2$ to about 500 mJ/cm$^2$ at a wavelength of about 365 nm. The unexposed portions of the photoresist are then developed with the appropriate solvent. For example, in the case of aqueous resists a dilute aqueous solution, e.g., a 0.5-1.5% sodium or potassium carbonate solution, is applied until desired patterns are obtained. The developing may be accomplished by immersing the substrate in the solution or spraying the solution on the substrate. The first conductive metal layer may then be further plated with the same or different metal using standard electroplating or electroless plating method until the desired circuit thickness in the range of about 5 nm to about 50 µm is achieved.

If desired, the dielectric substrate may be etched to form features in it by applying, crosslinking, and developing a pattern of photoresist, then placing the circuit into a bath of concentrated base at a temperature of from about 50° C. to about 120° C., which etches the portions of the polymeric film not covered by the crosslinked resist. This exposes certain areas of the original thin conductive metal layer. The resist is then stripped off both sides of the laminate in a 2-5% solution of an alkaline metal hydroxide at from about 20° C. to about 80° C., preferably from about 20° C. to about 60° C. Subsequently, the original thin first conductive layer is etched where exposed with an etchant which does not harm the polymeric film, e.g., a triiodide based etchant for Au available under the trade designation GE-8148 etchant from Transene Company Inc., (Danvers, Mass.). Alternatively, the patterning of the conductive layer may be achieved by selective deposition of conductive material, laser ablation, chemical etching, laser scribing, or any other suitable method. The final thickness of the metal layers (after all process steps have been completed) may be about 5 nm to about 50 µm thick.

Patterned insulator material may be formed on the circuit by a selective coating process such as screen printing or inkjet printing, lamination of a precut insulating material, or strips of insulating material, or lamination of a uniform sheet of insulating material followed by precise removal of selected sections using methods such as precision slitting, kiss cutting, etching or laser ablation which are widely known in the art. Alternatively, the insulative material may be a photoimageable material that can be precisely patterned by standard photolithographic techniques.

If desired, conventional converting steps may be used to take a continuous web of circuits for the sensors and separate them into smaller strips. Alternatively, the electrode circuits may be provided in a continuous web form to undergo post-processing steps that add the additional layers necessary to make a functioning electrochemical sensor.

Various modifications and alterations of this invention will become apparent to those skilled in the art without departing from the scope and spirit of this invention and it should be understood that this invention is not to be unduly limited to the illustrative embodiments set forth herein.

The invention claimed is:

1. An article comprising
an electrochemical sensor comprising
a substrate,
a conductive layer comprising at least one working electrode having a main body section, a connective neck section, and a terminal neck section, wherein the width of at least a portion of each electrode neck section is less than the width of the narrowest portion of the main body section, and
an insulative layer over a portion of the conductive layer such that at least a portion of each electrode neck section is covered by the insulative layer and a portion is not covered by the insulative layer.

2. The article of claim 1 wherein the width of the narrowest portion of the neck section is less than half the width of the narrowest portion of the main body section.

3. The article of claim 1 wherein the width of the narrowest portion of the neck section is less than one-tenth the width of the narrowest portion of the main body section.

4. The article of claim 1 wherein one or more neck is rectangular in shape.

5. The article of claim 1 wherein one or more neck is tapered in shape.

6. The article of claim 5 wherein the taper is linear.

7. The article of claim 5 wherein the taper is curved.

8. The article of claim 1 wherein the conductive layer includes at least a second electrode having a neck section.

9. The article of claim 1 wherein the conductive layer is comprised of a metal selected from the group consisting of gold, palladium, platinum, or alloys thereof.

10. The article of claim 1 wherein the conductive layer is about 5 nm to about 50 µm thick.

11. The article of claim 1 wherein the insulative layer is screen-printed, photolithographically patterned, or laminated.

12. The article of claim 1 wherein the substrate is made from a material selected fro the group consisting of liquid crystal polymer, poly(vinyl chloride), poly(ester), poly(olefin), (poly)imide, or (poly)carbonate.

13. An article comprising a glucose sensor test strip comprising the electrochemical sensor of claim 1.

14. An article comprising a glucose test kit comprising the glucose sensor strip of claim 13 and a meter.

15. The article of claim 1 comprising multiple electrodes wherein the main body sections of the electrodes are aligned.

16. A method for minimizing variations in the surface area of an electrode in an electrochemical sensor comprising
placing on a substrate a pattern of conductive material to form at least one working electrode having a main body section, a connective neck section, and a terminal neck section, wherein the width of at least a portion of each electrode neck section is less than the width of the narrowest portion of the main body section, and
placing over the conductive material a pattern of insulative material having an opening wherein at least a portion of each electrode neck section is exposed through the opening and a portion is covered by the insulative material,
each electrode neck section being of sufficient length that the placement accuracy of the insulative material with respect to the main electrode body can vary without the variance causing the insulative material to cover all of or none of each electrode neck.

* * * * *

UNITED STATES PATENT AND TRADEMARK OFFICE
CERTIFICATE OF CORRECTION

PATENT NO. : 7,294,246 B2 Page 1 of 1
APPLICATION NO. : 10/702828
DATED : November 13, 2007
INVENTOR(S) : Douglas B. Gundel It is certified that error appears in the above-identified patent and that said Letters Patent is hereby corrected as shown below:

Column 4
Line 45, delete "$_{oL}$" and insert -- $\sigma_L$ --, therefor
Line 47, delete "$_{oA}$" and insert -- $\sigma_A$ --, therefor
Line 49, after "processes)" insert -- . --, therefor Column 5
Line 20 (approx.), delete "[" and insert -- [ --, therefor Line 20 (approx.), delete "]" and insert -- ] --, therefor Column 8
Line 33, In Claim 12, delete "fro" and insert -- from --, therefor Signed and Sealed this First Day of April, 2008

JON W. DUDAS
*Director of the United States Patent and Trademark Office*